United States Patent [19]
Solovay

[11] Patent Number: 5,843,161
[45] Date of Patent: Dec. 1, 1998

[54] ENDOPROSTHESIS ASSEMBLY FOR PERCUTANEOUS DEPLOYMENT AND METHOD OF DEPLOYING SAME

[75] Inventor: Kenneth Solovay, Fort Lauderdale, Fla.

[73] Assignee: Cordis Corporation, Miami Lake, Fla.

[21] Appl. No.: 668,345

[22] Filed: Jun. 26, 1996

[51] Int. Cl.$^6$ .................................................. A61F 2/06
[52] U.S. Cl. .......................... 623/1; 606/191; 606/192; 606/194; 606/96; 623/12
[58] Field of Search ..................... 623/1, 11, 12, 623/66, 900, 108, 155; 606/191–200; 604/96, 104; 600/36; 424/426

[56] References Cited

U.S. PATENT DOCUMENTS

| | | | |
|---|---|---|---|
| 4,676,229 | 6/1987 | Krasnicki et al. | 128/4 |
| 4,733,665 | 3/1988 | Palmaz . | |
| 4,776,337 | 10/1988 | Palmaz | 623/1 |
| 4,878,906 | 11/1989 | Lindmann et al. . | |
| 4,950,227 | 8/1990 | Savin et al. . | |
| 5,019,090 | 5/1991 | Pinchuk . | |
| 5,123,917 | 6/1992 | Lee . | |
| 5,135,536 | 8/1992 | Hillstead . | |
| 5,163,951 | 11/1992 | Pinchuk et al. . | |
| 5,282,824 | 2/1994 | Gianturco . | |
| 5,330,500 | 7/1994 | Song . | |
| 5,360,443 | 11/1994 | Barone et al. | 623/1 |
| 5,366,504 | 11/1994 | Andersen et al. | 623/1 |
| 5,443,499 | 8/1995 | Schmitt . | |
| 5,476,506 | 12/1995 | Lunn . | |
| 5,522,883 | 6/1996 | Slater et al. | 623/1 |
| 5,527,353 | 6/1996 | Schmitt . | |
| 5,562,725 | 10/1996 | Schmitt et al. . | |
| 5,569,295 | 10/1996 | Lam | 623/1 |
| 5,569,463 | 10/1996 | Helmus et al. | 424/426 |
| 5,571,170 | 11/1996 | Palmaz et al. | 623/1 |
| 5,643,309 | 7/1997 | Myler et al. . | |
| 5,683,451 | 11/1997 | Lenker et al. | 623/1 |

OTHER PUBLICATIONS

C.T. Dotter, *Investigative Radiology*, 9:329–332 (1969).
Advanced Polymers Incorporated, Salem, NH, product specification brochure for heat shrink tubing, one page (publicly available prior to Jun. 26, 1996).
Cordis Corporation, Miami Lakes, FL, Instructions for Use: Sheath Introducer System, 24 pages (May 1994).
PolyMedica Biomaterials, Inc., Woburn, MA, ChronoFlex® Biodurable Medical–Grade Elastomers, Technical Fact Sheet, two pages (publicly available prior to Jun. 26, 1996).
Thermedics Inc., Woburn, MA, Carbothane™ Polycarbonate–based Aliphatic Polyurethanes product specification, one page (publicly available prior to Jun. 26, 1996).
Williams, David F., *Biocompatibility of Clinical Implant Materials*, vol. II, CRC Press, Inc., Boca Raton, FL, pp. 177–207 (1981).

*Primary Examiner*—David H. Willse
*Assistant Examiner*—Francis K. Cuddihy
*Attorney, Agent, or Firm*—Watts, Hoffmann, Fisher & Heinke, Co., L. P. A.

[57] ABSTRACT

The present invention provides an endoprosthesis assembly having a reduced cross sectional profile for percutaneous deployment and implantation within a body passageway such as a blood vessel. The assembly comprises a radially expandable cylindrical frame having first and second ends, and a first unexpanded outer diameter and a second expanded outer diameter. The assembly further comprises a radially expandable elastomeric sleeve surrounding a length of the frame and having first and second ends and a first unexpanded inner diameter and a second expanded inner diameter. The inner diameter of the expanded sleeve is not greater than the outer diameter of the expanded frame. The second expanded inner diameter of the sleeve is in a range from about 60% to about 380% greater than the first unexpanded inner diameter of the sleeve. The assembly of the preferred embodiment is adapted to be deployed through an introducer smaller than 9 French and the sleeve is capable of expanding to an inner diameter of about 12 millimeters.

32 Claims, 4 Drawing Sheets

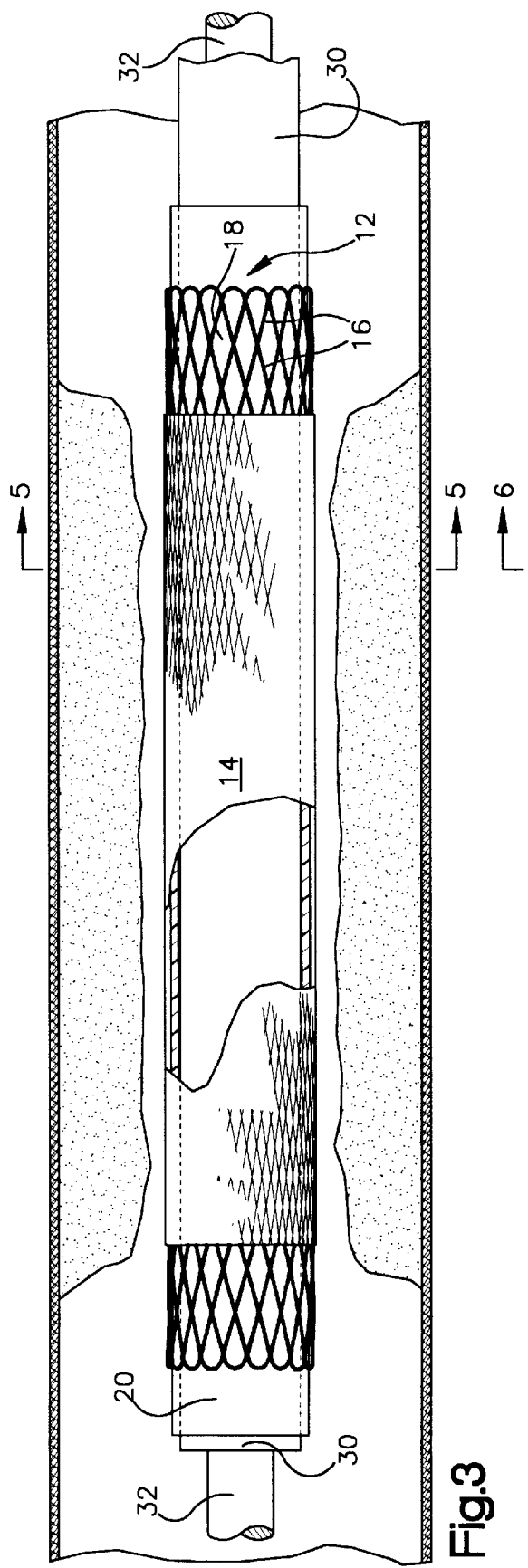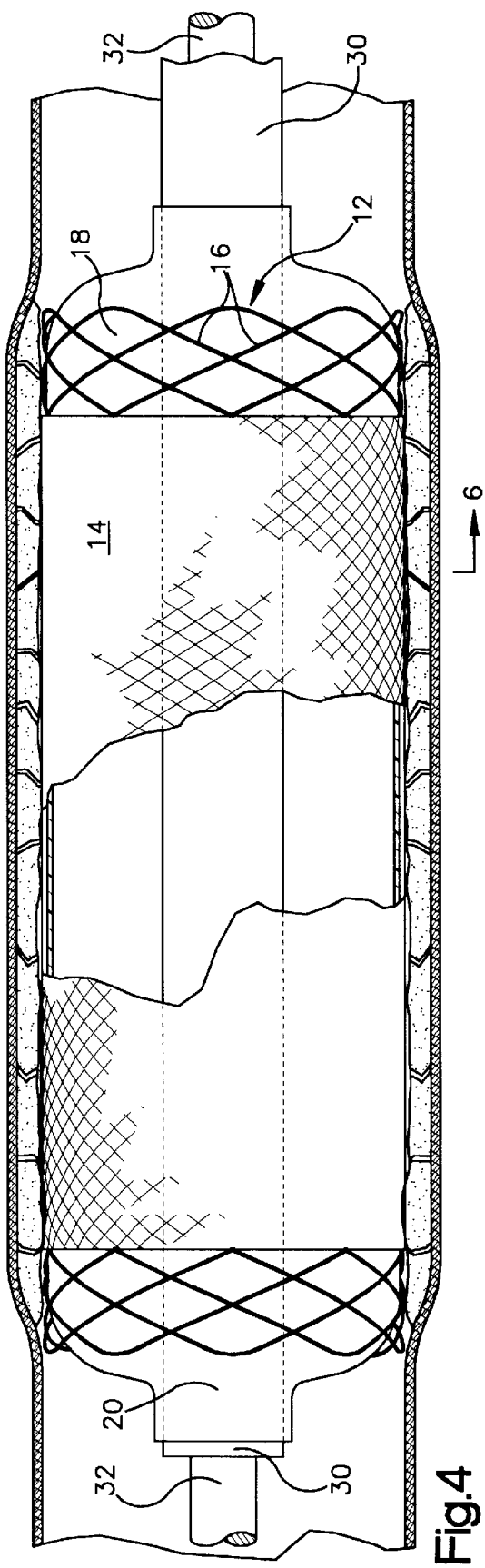

ENDOPROSTHESIS ASSEMBLY FOR PERCUTANEOUS DEPLOYMENT AND METHOD OF DEPLOYING SAME

FIELD OF THE INVENTION

This invention generally relates to an endoprosthesis assembly for percutaneous deployment and implantation into a blood vessel or other hollow body passageway, and a method for deploying an endoprosthesis assembly. More particularly, the invention relates to an assembly comprising a frame surrounded by an elastomeric sleeve, where the assembly has a reduced profile for percutaneous deployment.

BACKGROUND OF THE INVENTION

Various endoprostheses, or stents, have been proposed or developed for use in association with angioplasty treatments and other medical procedures wherein devices having expandable components are used to treat a condition within a body passageway such as a blood vessel. The stent is typically cylindrical or tubular in shape and has an open construction such as a scaffold, or frame. Stents are constructed so as to be radially collapsible. They are also radially expandable using techniques such as the introduction of a radially projecting force from inside the stent.

Stents for implantation into a blood vessel, artery or the like to maintain or restore the patency of the passageway have been deployed percutaneously to minimize the invasiveness associated with surgical exposure of the treatment site. Percutaneous deployment is initiated by an incision into the vasculature of the patient, typically into the femoral artery. An introducer comprising a cylinder open at each end is disposed across the incision to establish a passageway from the exterior of the artery to the interior of the artery. The introducer passageway includes a valve to block blood flow out of the artery. One end of a guide wire is passed through the introducer into the vasculature. The wire is threaded through the vasculature until the inserted end reaches the treatment site. The opposing end of the guide wire extends outside the introducer. A collapsed stent is crimped onto a deflated balloon connected to one end of an elongated flexible tube, or catheter. The crimped stent is deployed by threading the balloon end of the catheter onto the exposed end of the guide wire, pushing the catheter through the introducer into the vessel and pushing the catheter along the wire until the balloon and stent reach the treatment site. At the treatment site, the balloon is inflated causing the stent to radially expand and assume its second implantation diameter. The outer diameter of the expanded stent is greater than the inner diameter of the blood vessel at the treatment site, effectively causing an interference fit between the stent and the blood vessel that inhibits migration of the stent. The balloon is deflated and withdrawn, along with the catheter and the wire. The introducer is then removed from the artery.

Typical peripheral vascular applications for stents require a second expanded diameter in a range between about 4 millimeters to about 12 millimeters.

Introducers are sized according to a unit system whereby 1 French is the equivalent of one-third of a millimeter. The introducer dimension referenced is the inner diameter of the introducer passageway. Therefore, a 9 French introducer is sized to receive an assembly for percutaneous deployment with a cross sectional profile no greater than 3 millimeters.

The introducer provides a passageway from the exterior environment into the vascular system. Reduction in the required size of the introducer results in a smaller entrance wound into the vascular system. A smaller entrance wound is desirable in order to minimize the necessity of surgically closing the incision once the introducer is removed. However, efforts to reduce the required size of the introducer are limited by the deployment cross sectional profile of the catheter, balloon and stent.

Typically the stent consists of two or more struts connected together into a radially collapsible and expandable frame. The struts define void areas upon expansion of the stent at the treatment site. Larger void areas can permit malignant tissue growth through the stent spaces into the body passageway, and can also allow undesired contact between the blood and damaged portions of the interior surface of the vessel. Stent coverings have been proposed to alleviate the problems associated with void areas. Conventional stent coverings greatly increase the cross sectional profile of the catheter, balloon and stent, necessitating the use of larger introducers. Larger introducers increase the risk that surgical closure of the entrance wound will be required and increase the risks associated with larger incisions.

One such covering consists of a sleeve having a predetermined outer diameter intended to be substantially the same as the inner diameter of the body passageway at the treatment site. For deployment, the sleeve is mechanically deformed around the collapsed stent by folding or bending the sleeve into a layered or bunched configuration about the stent. The assembly of stent and sleeve is then crimped onto the balloon catheter and inserted through the introducer passageway into the vasculature and pushed to the treatment site.

The folded sleeve creates an uneven, bulky profile for the assembly that compromises easy insertion of the assembly through the introducer and prevents the use of an introducer having a reduced size. Further difficulties arise from the necessity of attaching the sleeve to the stent, by stitching, gluing or other time-consuming and labor intensive procedures.

The folded sleeve must also be maintained in the collapsed configuration during insertion and deployment. This is typically achieved by using a deployment sheath to constrain the folded sleeve. The sheath is then withdrawn at the treatment site, prior to inflation of the balloon. The sheath adds an additional dimension to the cross sectional profile of the assembly, further limiting the ability to restrict the size of the required introducer.

The deployment cross sectional profile of conventional covered stent assemblies capable of a second expanded diameter in a range between about 4 millimeters to about 12 millimeters requires the use of a 9 French introducer or larger. The size of the required introducer determines the size of the incision at the access site. Larger incisions increase the likelihood that surgical closure will be required. Even if surgical closure is avoided, larger incisions increase the potential for developing hematomas and other bleeding complications.

The predetermined and fixed diameter of the conventional sleeve does not allow for any miscalculation in the required size. If the predetermined and fixed diameter is too small, the fully unfolded sleeve will block the assembly from engaging the interior surface of the passageway. If the fully unfolded sleeve is too large, the sleeve will bunch between the stent and the interior surface of the passageway. Further, some porosity in the assembly may be desired, with pores of sufficient size to allow cellular ingrowth and capillary formation but small enough to prevent intrusions into the passageway as discussed above.

There remains a need for a covered stent assembly with a covering that does not contribute significantly to the overall cross sectional profile of the assembly, allowing for the use of smaller introducers to reduce the risk that surgical closure of the entry wound will be required and to reduce the potential for bleeding complications. There is also a need for a covered stent assembly with a covering that maintains its position relative to the stent without the need for stitching, gluing or otherwise attaching the covering to the stent. There is further a need for a covered stent assembly with a covering that does not require a precise prior determination of the second expanded diameter of the covering. Finally, there remains a need for a stent covering providing the above advantages that can be used with stents capable of a second expanded diameter in a range from about 4 millimeters to about 12 millimeters.

SUMMARY OF THE INVENTION

The present invention provides an endoprosthesis assembly for percutaneous deployment and implantation within a body passageway, comprising a radially expandable cylindrical frame and an elastomeric covering. The covering, or sleeve, avoids the problems associated with the void spaces of a bare stent, without contributing significantly to the cross sectional profile of the assembly. Rather than assuming a fixed diameter prior to deployment, the elastomer sleeve assumes a first unexpanded diameter while the assembly is pushed through the introducer, and a second expanded diameter at the treatment site resulting from the expansion of the stent. The elastomeric sleeve is strong enough to withstand the stress associated with expansion of the stent to the second expanded diameter, and is compliant enough to avoid collapsing the stent after the expansion is complete. The deployment cross sectional profile of the assembly of the present invention allows a smaller introducer or other insertion device to be used than was previously possible using traditional coverings, minimizing the trauma at the introduction site and reducing the risk that surgical closure of the entry wound will be required.

Design features, such as porosity and wall thickness, as well as manufacturing techniques such as braiding, can be employed to increase the compliance of the expanded sleeve of the present invention and assure that the sleeve can be expanded within the required range without collapsing the expanded stent.

In accordance with the above, the present invention provides for an endoprosthesis assembly for percutaneous deployment and implantation within a body passageway, comprising a radially expandable cylindrical frame having first and second ends, a first unexpanded outer diameter and a second expanded outer diameter. The assembly further comprises a radially expandable elastomeric sleeve surrounding a length of the frame and having first and second ends, a first unexpanded inner diameter and a second expanded inner diameter. A second expanded inner diameter of the sleeve is not greater than a second expanded outer diameter of the frame. A second expanded inner diameter of the sleeve is in a range from about 60% to about 380% greater than a first unexpanded inner diameter of the sleeve. The sleeve expands to a second expanded diameter without causing the expanded frame to collapse. In the preferred embodiment, a first unexpanded inner diameter of the sleeve is not greater than a first unexpanded outer diameter of the frame, so that at least a portion of the unexpanded sleeve grips the unexpanded frame prior to crimping onto the catheter.

In the preferred embodiment of the present invention, the expanded sleeve has a sleeve modulus in a range from about 100 psi to about 6000 psi, and a second expanded inner diameter in a range from about 4 millimeters to about 12 millimeters. The frame hoop strength is about 30 psi at an expanded diameter of about 4 millimeters, and about 6 psi at an expanded diameter of about 12 millimeters. The unexpanded sleeve wall thickness is in a range from about 0.002 inches to about 0.005 inches, most preferably 0.005 inches.

The sleeve of the preferred embodiment comprises an elastomer having a percent elongation at break in a range from about 500 to about 585, an ultimate tensile strength in a range from about 4400 to about 5300 pounds per square inch, and a durometer hardness in a range from about 73 (shore A) to about 80 (shore A). One such elastomer is a polycarbonate polyurethane. The assembly of the preferred embodiment is adapted to be disposed through an introducer having an inner diameter in a range from about 2.5 mm. to about 2.7 mm.

The compliance of the sleeve of the present invention can be adjusted by the use of various textile methods, such as braiding, knitting or weaving the sleeve from yarn spun from the elastomeric material. In the preferred embodiment, the sleeve is braided directly onto a frame that has assumed a first unexpanded diameter. The denier of the yarn is preferably in a range from about 10 to about 70, and is most preferably 40.

The present invention provides a method of percutaneously deploying an endoprosthesis assembly for implantation at a treatment site within a body passageway of a patient, comprising the steps of forming the assembly by surrounding a length of an unexpanded cylindrical frame having a first unexpanded outer diameter with an elastomeric sleeve having a first unexpanded inner diameter, crimping the unexpanded assembly onto a first end of an elongated flexible tube, or catheter, inserting the assembly inside the passageway, threading the catheter through the interior of the passageway until the first end of the catheter reaches the treatment site, expanding the frame to a second expanded outer diameter, and expanding the sleeve to a second expanded inner diameter not greater than a second expanded outer diameter of said frame and a second expanded outer diameter not less than the inner diameter of the body passageway.

These and other advantages and features of this invention will be clearly understood through consideration of the following detailed description of alternate embodiments of the invention in conjunction with the accompanying drawings.

BRIEF DESCRIPTION OF THE DRAWINGS

FIG. 1 illustrates the catheter after one end has been threaded onto a guide wire and pushed through the introducer into the vasculature.

FIG. 3 is a side view partially cut away and partially in section of the assembly, balloon, catheter and guide wire inside a blood vessel prior to inflation of the balloon.

FIG. 4 is a side view partially cut away and partially in section of the assembly, balloon, catheter and guide wire inside a blood vessel after inflation of the balloon.

DESCRIPTION OF THE PREFERRED EMBODIMENT

Figure 1:
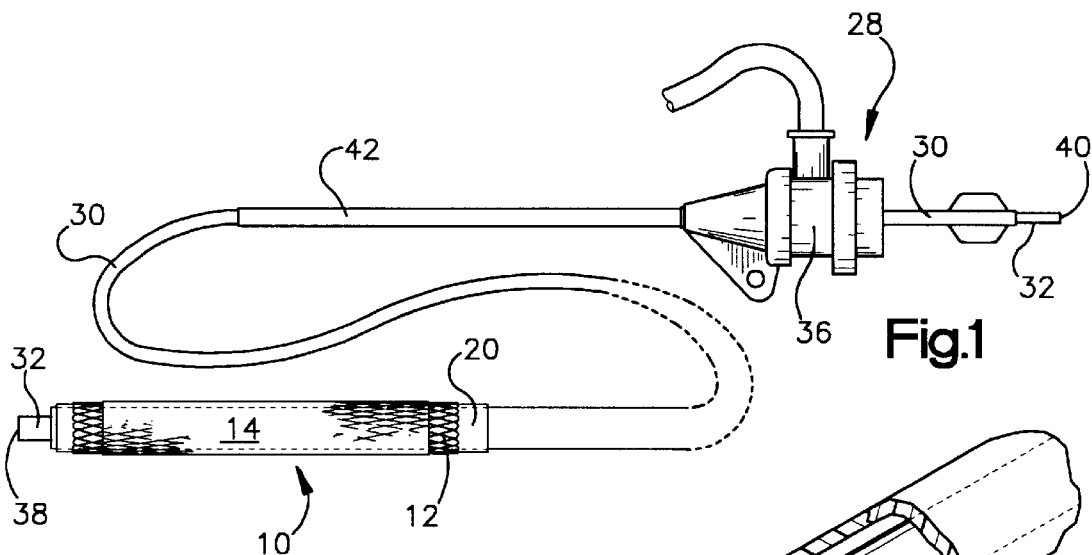
FIG. 1 is a depiction of the unexpanded assembly (enlarged) crimped onto a balloon attached to the end of a catheter.

The present invention provides for an endoprosthesis assembly 10 for percutaneous deployment and implantation within a body passageway, comprising a radially expandable cylindrical frame 12 having first and second ends, a first unexpanded outer diameter and a second expanded outer diameter. The assembly 10 further comprises a radially expandable elastomeric sleeve 14 surrounding a length of the frame 12. The sleeve 14 has first and second ends, a first unexpanded inner diameter and a second expanded inner diameter. The inner diameter of the expanded sleeve 14 is not greater than the outer diameter of the expanded frame. The second expanded inner diameter of said sleeve 14 is in a range from about 60% to about 380% greater than said first unexpanded inner diameter of said sleeve.

The frame 12 has an open structure comprised of support members 16, or struts, joined to enable the frame to radially expand and collapse. The support members define void spaces 18 that expand as the frame expands. (FIGS. 3 and 4.) The support members 16 form a generally cylindrical shape with a longitudinal axis. The frame 12 of the preferred embodiment comprises a stent manufactured from support members 16 consisting of tantalum wires having a diameter of 0.007 inches. Such stents are known and disclosed, for example, in Pinchuk, U.S. Pat. No. 5,019,090, incorporated herein by reference. In the preferred embodiment, expansion of the stent to the second expanded diameter is achieved by inflation of a percutaneous transluminal angioplasty balloon 20 on which the stent 12 has been crimped. It will be appreciated, however, that a stent expandable by alternate methods, such as self-expanding stents and thermally expanding stents, is within the scope of the present invention. In one preferred embodiment of the present invention, the assembly 10 can assume a first unexpanded diameter of approximately 2 millimeters, and expand to a second diameter in a range from about 4 millimeters to about 7 millimeters. The stent 12 of this embodiment has a hoop strength ranging from about 30 pounds per square inch to about 18 pounds per square inch., respectively. Alternatively, the assembly 10 can be crimped to a first unexpanded diameter of approximately 2.54 millimeters, and expanded to a second diameter in a range from about 8 millimeters to about 12 millimeters. The stent of this embodiment has a hoop strength ranging from about 18 pounds per square inch to about 6 pounds per square inch, respectively.

"Hoop strength" as used herein refers to the intraluminal force exerted by the expanded stent 12. This force is measured by expanding a stent within a latex tube (not shown). The pressure surrounding the exterior of the tube is gradually increased until the expanded stent collapses. The pressure at collapse is denominated the "hoop strength" of the stent. It is generally appreciated by those skilled in the art that hoop strength is a function of the amount of expansion undergone by the stent. Therefore, a stent capable of expansion to a range of diameters has a corresponding range of hoop strengths. Typically, hoop strength and expanded stent diameter are inversely proportional.

Figure 7:
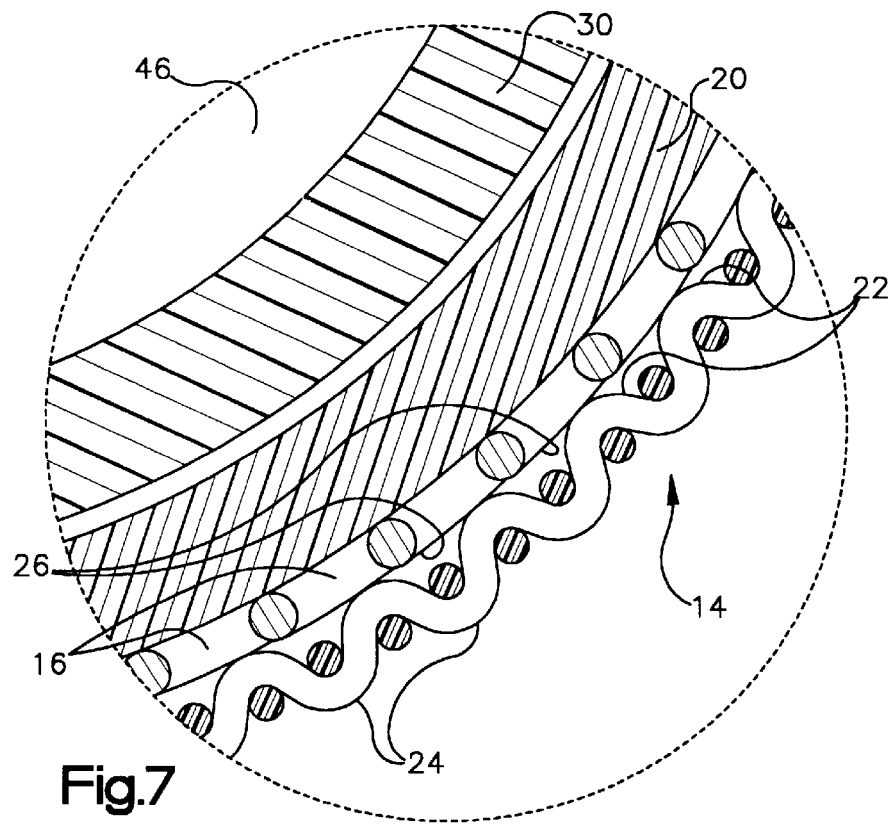
FIG. 7 is a detail of a portion of FIG. 5 as indicated therein.
Figure 8:
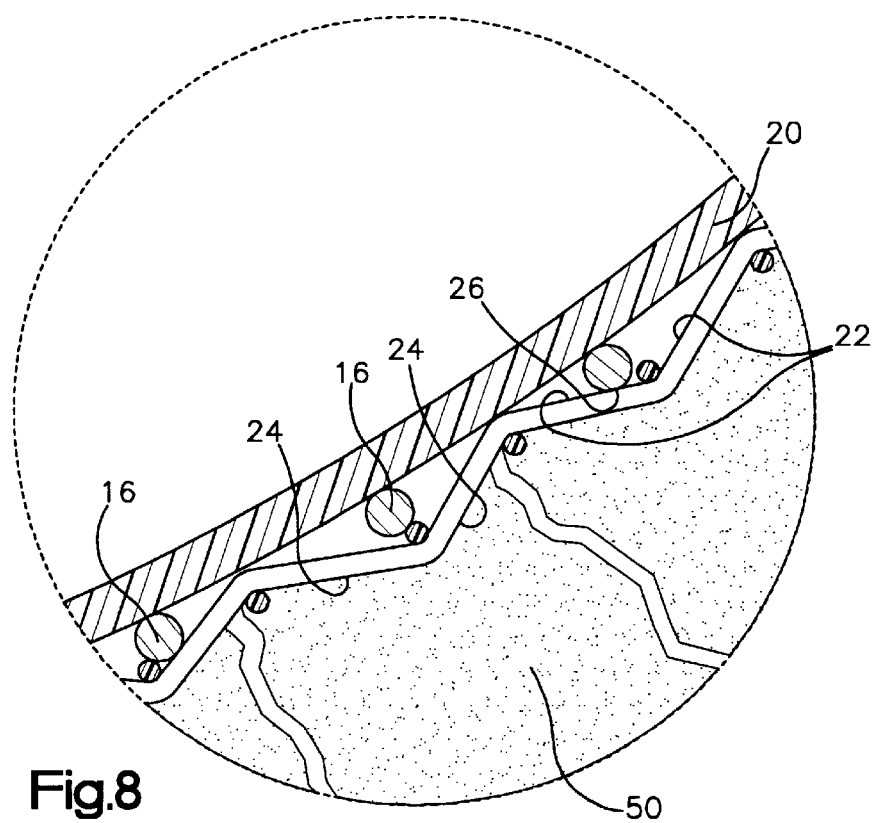
FIG. 8 is a detail of a portion of FIG. 6 as indicated therein.

The elastomeric sleeve 14 of the preferred embodiment concentrically surrounds a longitudinal extent of the stent 12. The sleeve 14 has an inner surface 22 and an outer surface 24 that define a sleeve wall. As can best be seen from the detail depictions of the preferred embodiment in FIGS. 7 and 8, the inner surface 22 of the unexpanded sleeve engages the outer surface 26 of the unexpanded stent 12. (FIG. 7.) The inner surface 22 of the expanded sleeve 14 engages the outer surface 26 of the expanded stent 12. (FIG. 8.) The close hugging fit between the unexpanded and expanded sleeve 14 and stent 12 of the preferred embodiment obviates the need for separate attachments to be formed between the sleeve and the stent and reduces the potential for separation of the sleeve 14 and stent 12 during deployment and implantation. It will be appreciated, however, that the unexpanded sleeve and stent can be attached by tacking, sewing or other methods known in the art if play exists between the unexpanded sleeve and the unexpanded stent, without departing from the intended scope of the present invention. The thickness of the sleeve wall is reduced as the sleeve 14 expands, creating a larger opening within the vessel at the treatment site than would otherwise be available with conventional stent coverings having a fixed wall thickness.

The sleeve 14 of the present invention has an unexpanded wall thickness in a range from about 0.002 to about 0.005 inches, preferably about 0.005 inches. The assembly 10 of the preferred embodiment allows a 7.5 French introducer 28 to be used with an assembly 10 expandable to a maximum second diameter of about 7 mm, and an 8 French introducer 28 to be used with an assembly 10 expandable to a maximum second diameter of about 12 mm. Conventional assemblies comprising a stent and a covering require the use of a 9 French introducer in the first instance and a 12 French introducer in the second. This reduction in the required introducer size achieved by the present invention is of particular significance, since it reduces the risk that surgical closure of the entrance wound will be required. The reduction in the required introducer size also reduces the risk of developing hematomas and other bleeding complications.

It is of particular significance in the present invention that the sleeve 14 of the preferred embodiment can expand to greater than 380% of its unexpanded first diameter without causing the underlying stent 12 to collapse once expansion to the second expanded diameter is achieved by balloon inflation or otherwise. The "sleeve modulus" is an expression of the tendency of the expanded sleeve to collapse the expanded stent. As used herein, "sleeve modulus" is the stress experienced by the sleeve at a given expansion divided by the strain, or expansion of the sleeve. In one aspect of the present invention, the range of sleeve modulii enabling the desired expansion without collapsing the expanded stent is believed to be related to the hoop strength of the expanded stent, the expanded diameter of the sleeve, the wall thickness of the sleeve at the expanded diameter, and the percent change in the sleeve diameter as follows:

$$\text{sleeve modulus} = \frac{\text{stent hoop strength} \times \text{sleeve I.D.}}{2 \times \text{sleeve wall thickness} \times \% \text{ change sleeve diameter}}$$

The sleeve modulus approximated using this expression is believed to be a maximum for the particular expanded stent hoop strength, expanded sleeve wall thickness, expanded sleeve diameter and percent change in sleeve diameter. Using the above relationship, it is believed the maximum sleeve modulus for a sleeve having an unexpanded wall thickness of 0.005 inches covering a stent having a minimum hoop strength of 4 psi is approximately 100 psi for an expanded sleeve diameter from about 60% to about 380% greater than the unexpanded sleeve diameter. At the other end of the range, it is believed that the maximum sleeve modulus for a sleeve having an unexpanded wall thickness of 0.002 inches covering a stent having a minimum hoop strength of 30 psi is approximately 6000 psi for an expanded sleeve diameter from about 60% to about 380% greater than the unexpanded sleeve diameter. It is believed that expanded sleeves having a sleeve modulus that exceeds the maximum sleeve modulus will cause the expanded stent to collapse.

The sleeve modulus range identified above facilitates the selection of a suitable elastomer material from which to manufacture the sleeve 14 of the present invention. The sleeve modulus can be manipulated if needed to fall within the modulus range identified above by design options such as reducing the thickness of the sleeve wall, adding porosity to the sleeve, or using conventional textile fabrication techniques such as braiding, weaving or knitting to manipulate the stress associated with the expansion of the sleeve.

In the preferred embodiment, the sleeve 14 is manufactured from a polycarbonate polyurethane resin having known biodurable characteristics. Other suitable elastomeric materials having a high elongation and a low modulus, such as silicones, can be used. In one aspect of the preferred embodiment the resin can be spun into a multi-filament yarn and braided into a sleeve 14. In another aspect of the preferred embodiment, the resin can be extruded into a porous tube or a film used to form a sleeve 14 which is then slipped over a stent 12. The following examples are intended to be illustrative, and are not intended to limit the scope of the present invention.

EXAMPLE 1

The polycarbonate polyurethane resin is spun into a multi-filament yarn. The yarn is braided into a sleeve. The properties of the polyurethane are identified:

| | |
|---|---|
| elongation at break: | 500% |
| ultimate tensile strength (psi): | 4400 |
| durometer hardness (shore A): | 73 |
| yarn denier: | 40 |
| sleeve wall thickness, unexpanded (in.): | .005 |

A resin with the properties identified is available under the trademark Carbothane from Thermedics, Inc., 470 Wildwood St., Woburn, Mass. 01888-1799.

Figure 9:
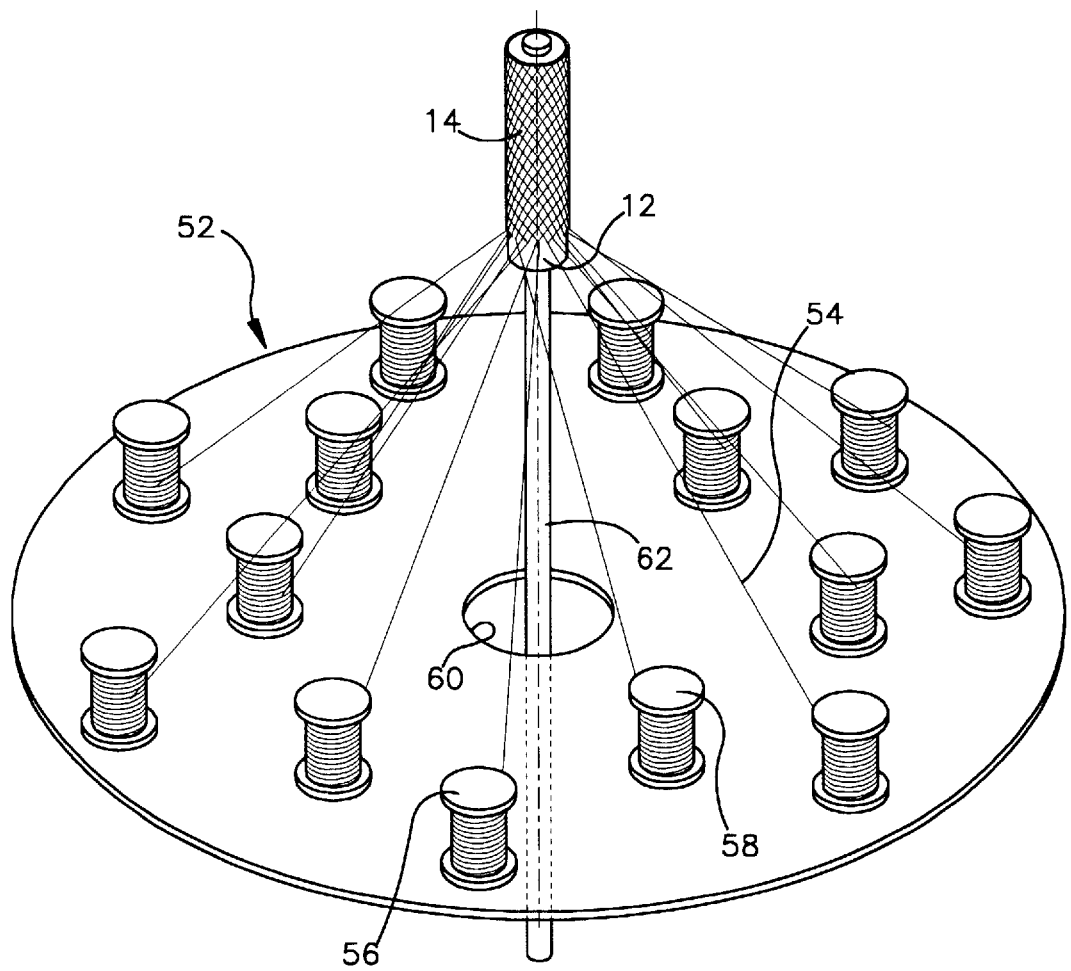
FIG. 9 is a schematic depiction of a machine for braiding a sleeve onto a stent to form the assembly.

FIG. 9 conceptually shows a braiding machine 52 that may be used to fabricate the sleeve 14. The sleeve 14 is braided directly onto the stent 12 as hereinafter described. The yarn 54 is wound onto eight bobbins 56 moving in a clockwise direction and eight bobbins 58 moving in a counter-clockwise direction. The bobbins 56, 58 are fitted onto sixteen carriers (not shown) on the braiding machine 52. The braiding machine 52 has an opening 60 for a mandrel 62. The sixteen carriers move the bobbins 56, 58 around the mandrel 62 in two opposing directions, eight clockwise 56 and eight counter-clockwise 58. The stent 12 is crimped on the mandrel 62 and passed through the center of the sixteen revolving yarn carriers as the carriers rotate at a set speed causing the yarn 54 to braid onto the outer surface 26 of the unexpanded stent 12. The braiding machine 52 provides several techniques to control the structure and properties of the braid, including the amount of tension in the yarn 54, the pitch of the braid, and the number of overbraids. After the braiding is completed the sleeve 14 may be annealed in an oven at 110° C. to relieve tension in the yarn 54, as well as to fuse overlapping yarns 54 together.

In another aspect of the preferred embodiment, the braiding is performed directly on the mandrel 62. The braided sleeve 14 is slid off of the mandrel 62 and cut to the desired length. The sleeve 14 is slightly expanded and the unexpanded stent 12 is placed within the slightly expanded sleeve 14. The sleeve 14 is then released allowing the sleeve 14 to contract or recoil onto the unexpanded stent 12 to form the assembly 10. The assembly 10 is slightly further crimped to the deflated balloon 20 attached to the catheter 30 prior to percutaneous deployment.

The preferred yarn denier ranges from about 10 to about 70, with 40 the most preferred denier.

EXAMPLE 2

The polycarbonate polyurethane resin is extruded into a tube or film. The tube is cut into a sleeve. The film is cut into strips, and opposing ends are fused or otherwise joined into a cylindrical sleeve. The properties of the polyurethane are identified:

| | |
|---|---|
| elongation at break: | 585% |
| ultimate tensile strength (psi): | 5300 |
| durometer hardness (shore A): | 80 |
| film thickness, unexpanded (in.): | .002 |
| tube wall thickness, unexpanded (in.): | .004 |

A resin with the properties identified is available under the trademark ChronoFlex available from Polymedica Biomaterials, Inc., 11 State Street, Woburn, Mass. 01801.

The extruded sleeve 14 is slid over an unexpanded stent 12 to form the assembly 10. The assembly 10 is slightly further crimped to the deflated balloon 20 attached to the catheter 30 prior to percutaneous deployment.

A sleeve 14 manufactured from extruded film or tubing of the material described above requires the incorporation of porosity into the extruded material to create a sleeve 14 that will expand to about 380% of its first unexpanded diameter without causing the expanded stent 12 to collapse. The addition of porosity reduces the sleeve modulus as discussed above. It will be appreciated that porosity can be incorporated into the extruded material without departing from the intended scope of the present invention. Porosity can be achieved by laser hole drilling after the extrusion is complete, or by the use of a polymer resin having particulate fillers that are later removed from the solid by chemical exposure or other techniques as are known in the art.

Figure 2:
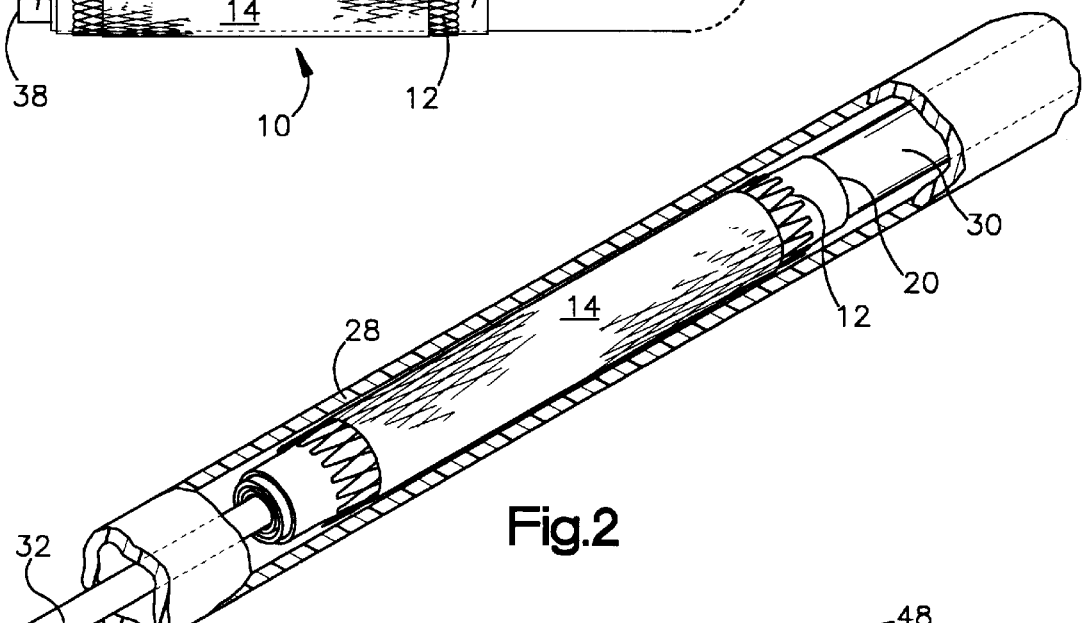
FIG. 2 is a perspective depiction of the assembly, balloon, catheter and guide wire inside the introducer.

The assembly 10 during deployment is depicted in FIG. 1. The assembly 10 has been crimped to the exterior of a deflated balloon 20. The first end region of a catheter 30 passes through the interior of the balloon 20 and is sealably connected thereto as is known. As depicted in FIG. 1, the first end 38 of a guide wire 32 has been inserted through an introducer 28 and pushed through the vasculature to the treatment site, while the second end 40 of the guide wire 32 extends outside the introducer 28. The introducer 28 includes a hub 36 defining a passageway into the vasculature and preventing blood flow out of the vasculature. A hollow tube, or sheath 42 extends from the hub into a portion of the vasculature. The first end region of the catheter has been enlarged in FIG. 1 to magnify the guide wire 32, catheter 30, balloon 20, stent 12 and sleeve 14. FIG. 2 illustrates the guide wire 32, catheter 30, deflated balloon 20, unexpanded stent 12 and sleeve 14 inside the introducer 28.

The length of the stent 12 is less than the length of the balloon 20. As can best be seen in FIG. 4, the stent 12 is positioned on the balloon 20 to avoid the ends of the balloon that taper to a sealed connection with the catheter 30 upon inflation. The sleeve 14 of the preferred embodiment does not foreshorten upon expansion. (FIGS. 3 and 4.)

Figure 5:
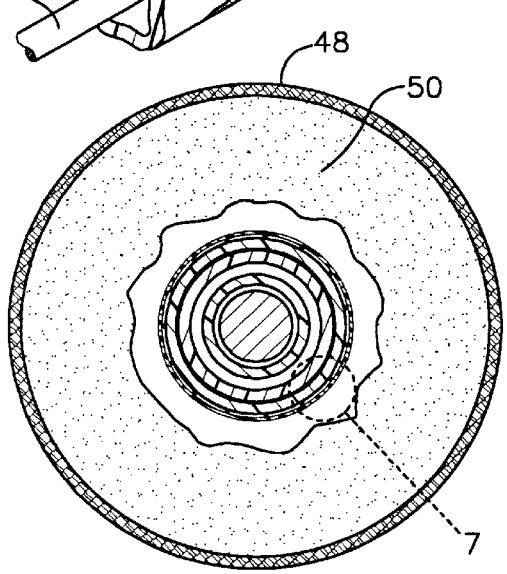
FIG. 5 is a cross sectional view as seen approximately from the plane indicated by the line 5—5 of FIG. 3.
Figure 6:
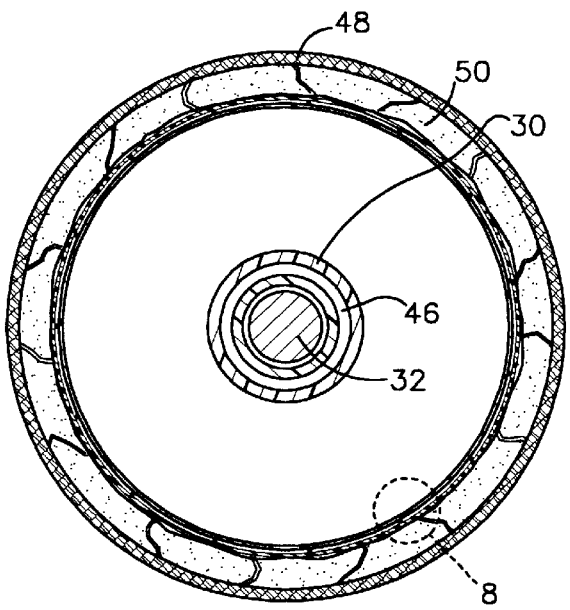
FIG. 6 is a cross sectional view as seen approximately from the plane indicated by the line 6—6 of FIG. 4.

The cross sectional profile of the balloon 20, catheter 30, and crimped stent 12 and sleeve 14 must be small enough to pass through the passageway provided by the introducer 28. (FIG. 2.) An opening in the first end region of the catheter to a guide wire conduit within the catheter is threaded onto the guide wire second end 40. The balloon 20, catheter 30, and unexpanded stent 12 and sleeve 14 are pushed through the introducer hub 36 and along the guide wire 32 until the assembly 10 reaches the treatment site. FIG. 5 is a cross section of the assembly 10 at the treatment site prior to inflation of the balloon 20. The vessel 48 is partially occluded by the presence of plaque 50. Fluid is introduced into a fluid conduit 46 of the catheter 30 and expands the balloon 20, compressing the plaque 50. (FIG. 6.) The inflated balloon 30 expands the stent 12 to a second diameter and the sleeve 14 to a second diameter. (FIGS. 4 and 6.) The fluid is then withdrawn, causing the balloon 20 to deflate. The catheter 30, balloon 20 and guide wire 32 are then withdrawn.

As can be seen in FIG. 8, the expanded sleeve exterior surface 24 engages the interior surface of the plaque 50. The sleeve compliance enables the expanded sleeve 14 to conform around the struts 16 of the expanded stent 12, creating an undulating outer surface of the assembly 10 implanted into the exposed surface of the plaque 50. This undulating outer surface of the expanded assembly increases the contact surface area between the obstructing tissue within the vessel and reduces the potential for migration of the assembly. While the preferred embodiment contemplates an assembly for deployment within the vasculature, it will be appreciated that the invention can be used to reinforce or restore the patency of other body passageways, such as the esophagus and trachea.

While the present invention has been described with a degree of particularity, it is the intent that the invention include all modifications and alterations from the disclosed design falling within the spirit and scope of the appended claims.

What is claimed is:

1. An endoprosthesis assembly for percutaneous deployment and implantation within a body passageway, comprising:
   a radially expandable cylindrical frame having first and second ends, said fame having a first unexpanded outer diameter and a second expanded outer diameter; and
   a radially expandable elastomeric sleeve surrounding a length of said frame and having first and second ends, said sleeve having a first unexpanded inner diameter and a second expanded inner diameter;
   wherein said second expanded inner diameter of said sleeve is not greater than said second expanded outer diameter of said frame;
   wherein said sleeve, when expanded, has a sleeve modulus in a range from about 100 psi to about 6000 psi; and
   wherein said second expanded inner diameter of said sleeve is in a range from about 60% to about 380% greater than said first unexpanded inner diameter of said sleeve.

2. The endoprosthesis assembly of claim 1, wherein said first unexpanded inner diameter of said sleeve is not greater than said first unexpanded outer diameter of said frame.

3. The endoprosthesis assembly of claim 1, wherein said second expanded inner diameter of said sleeve is in a range from about 4 mm to about 12 mm.

4. The endoprosthesis assembly of claim 1, wherein said sleeve comprises an elastomer having a percent elongation at break in a range from about 500 to about 585, an ultimate tensile strength in a range from about 4400 psi to about 5300 psi, and a durometer hardness in a range from about 73 (shore A) to about 80 (shore A).

5. The endoprosthesis assembly of claim 2, wherein said sleeve comprises an elastomer having a percent elongation at break in a range from about 500 to about 585, an ultimate tensile strength in a range from about 4400 psi to about 5300 psi, and a durometer hardness in a range from about 73 (shore A) to about 80 (shore A).

6. The endoprosthesis assembly of claim 3, wherein said sleeve comprises an elastomer having a percent elongation at break in a range from about 500 to about 585, an ultimate tensile strength in a range from about 4400 psi to about 5300 psi, and a durometer hardness in a range from about 73 (shore A) to about 80 (shore A).

7. The endoprosthesis assembly of claim 1, wherein said sleeve comprises a polycarbonate polyurethane.

8. The endoprosthesis assembly of claim 2, wherein said sleeve comprises a polycarbonate polyurethane.

9. The endoprosthesis assembly of claim 3, wherein said sleeve comprises a polycarbonate polyurethane.

10. The endoprosthesis assembly of claim 1, wherein said assembly is adapted to be disposed through an introducer having an inner diameter in a range from about 2.5 mm to about 2.7 mm.

11. The endoprosthesis assembly of claim 10, wherein said second expanded inner diameter of said sleeve is in a range from about 4 mm to about 7 mm.

12. The endoprosthesis assembly of claim 10, wherein said second expanded inner diameter of said sleeve is in a range from about 7 mm to about 12 mm.

13. The endoprosthesis assembly of claim 1, wherein said sleeve is braided from yarn spun from elastomeric material.

14. The endoprosthesis assembly of claim 1, wherein said sleeve is knitted from yarn spun from elastomeric material.

15. The endoprosthesis assembly of claim 1, wherein said sleeve is woven from yarn spun from elastomeric material.

16. The endoprosthesis assembly of claim 13, wherein said yarn has a denier in a range from about 10 to about 70.

17. The endoprosthesis assembly of claim 14, wherein said yarn has a denier in a range from about 10 to about 70.

18. The endoprosthesis assembly of claim 15, wherein said yarn has a denier in a range from about 10 to about 70.

19. The endoprosthesis assembly of claim 1, wherein said sleeve, when unexpanded, has a wall thickness in a range from about 0.002 inches to about 0.005 inches and wherein said frame has a hoop strength in a range from about 6 psi to about 30 psi.

20. A method of percutaneously deploying an endoprosthesis assembly for implantation at a treatment site within a body passageway of a patient, comprising the steps of:
   (a) forming said assembly by surrounding a length of an unexpanded cylindrical fame having a first unexpanded outer diameter with an elastomeric sleeve having a first unexpanded inner diameter;
   (b) inserting said assembly into said body passageway;
   (c) threading said assembly through said body passageway until said assembly reaches said treatment site; and
   (d) expanding said frame to a second expanded outer diameter such that said sleeve is expanded to a second expanded inner diameter not greater than said second expanded outer diameter of said frame and such that said sleeve is expanded to a second expanded outer diameter not less than an inner diameter of said body passageway at said treatment site, wherein said sleeve, when expanded, has a sleeve modulus in a range from about 100 psi to about 6000 psi and wherein said second expanded inner diameter of said sleeve is in a range from about 60% to about 380% greater than said first unexpanded inner diameter of said sleeve.

21. The method of claim 20, wherein said inserting step (b) comprises the step of pushing said assembly through an introducer.

22. The method of claim 21, wherein said introducer has an inner diameter in a range from about 2.5 mm to about 2.7 mm.

23. The method of claim 20, wherein said expanding step (d) comprises the step of inflating a balloon disposed inside said frame.

24. The method of claim 22, wherein said introducer is a 7.5 French introducer and wherein said second expanded inner diameter of said sleeve is in a range from about 4 mm to about 7 mm.

25. The method of claim 22, wherein said introducer is an 8 French introducer and wherein said second expanded inner diameter of said sleeve is in a range from about 8 mm to about 12 mm.

26. The method of claim 20, wherein said first unexpanded inner diameter of said sleeve is not greater than said first unexpanded outer diameter of said frame.

27. The method of claim 20, additionally comprising the step of crimping said assembly onto a first end of an elongated flexible tube for insertion of said assembly into said body passageway and for threading said assembly through said body passageway.

28. The method of claim 20, wherein said sleeve comprises an elastomer having a percent elongation at break in a range from about 500 to about 585, an ultimate tensile strength in a range from about 4400 psi to about 5300 psi, and a durometer hardness in a range from about 73 (shore A) to about 80 (shore A).

29. The method of claim 20, wherein said sleeve comprises a polycarbonate polyurethane.

30. The method of claim 20, wherein said sleeve is braided, knitted, or woven from yarn spun from elastomeric material.

31. The method of claim 30, wherein said yarn has a denier in a range from about 10 to about 70.

32. The method of claim 20, wherein said sleeve, when unexpanded, has a wall thickness in a range from about 0.002 inches to about 0.005 inches and wherein said frame has a hoop strength in a range from about 6 psi to about 30 psi.

* * * * *